United States Patent [19]
Kametani

[11] 3,933,826
[45] Jan. 20, 1976

[54] PROTOBERBERINE DERIVATIVES

[75] Inventor: Tetsuji Kametani, Sendai, Japan

[73] Assignee: Nippon Chemiphar Co., Ltd., Tokyo, Japan

[22] Filed: Nov. 20, 1973

[21] Appl. No.: 417,492

[30] Foreign Application Priority Data
Nov. 20, 1972 Japan............................ 47-115706

[52] U.S. Cl......... 260/287 C; 260/289 CF; 424/258
[51] Int. Cl.²...................................... C07D 215/16
[58] Field of Search..................... 260/287 R, 287 C

[56] References Cited
UNITED STATES PATENTS
3,420,834   1/1969   Muller et al. .................. 260/287 R

*Primary Examiner*—Raymond V. Rush
*Assistant Examiner*—David E. Wheeler
*Attorney, Agent, or Firm*—Oblon, Fisher, Spivak, McClelland & Maier

[57] ABSTRACT

Protoberberine derivatives having the general formula:

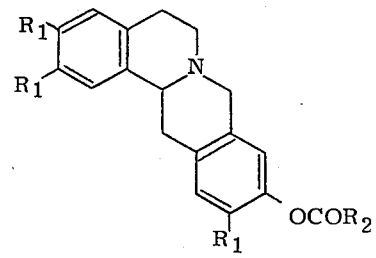

wherein $R_1$ is a lower alkoxy group, i.e. $C_1$ to $C_5$ alkoxy; $R_2$ is a lower alkyl group, i.e. $C_1$ to $C_5$ alkyl, pyridyl group, phenyl group substituted by two or three lower alkoxy groups, i.e. $C_1$ to $C_5$ alkoxy or a phenylvinyl group substituted by two or three lower alkoxy groups, i.e. $C_1$ to $C_5$ alkoxy; having excellent analgesic, vasodilating and hypotensive effects and are prepared from know protoberberines by reaction with carobxylic acids.

1 Claim, No Drawings

PROTOBERBERINE DERIVATIVES

BACKGROUND OF THE INVENTION

1. Field of the Invention

This invention relates to protoberberine derivatives represented by the following formula (I):

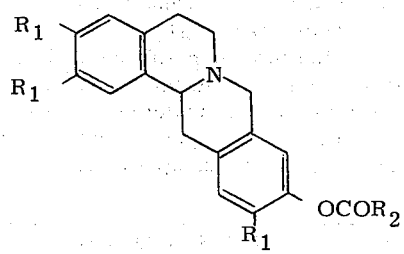

wherein $R_1$ is a lower alkoxy group; i.e. $C_1$ to $C_5$ alkoxy; $R_2$ is a lower alkyl group, i.e. $C_1$ to $C_5$ alkyl, pyridyl group, phenyl group substituted by two or three lower alkoxy groups, i.e. $C_1$ to $C_5$ alkoxy or a phenyl-vinyl group substituted by two or three lower alkoxy groups, i.e. $C_1$ to $C_5$ alkoxy and to a process for producing the novel protoberberine derivatives of the above formula (I).

2. Description of the Prior Art

It has been known that some of the protoberberine derivatives, such as 5, 6, 13, 13a-tetrahydro-2, 3, 10, 11-tetramethoxy-8H-dibenzo [a, g] quinolizine have analgesic, vasodilating and hypotensive effects.

However, the known protoberberine derivatives to not exhibit in many cases sufficiently high analgesic, vasodilating and hypotensive effects and in addition, they exert a depressive effect on the central nervous system.

SUMMARY OF THE INVENTION

Accordingly, one object of this invention is to provide novel protoberberine derivatives which possess very high analgesic, vasodilating and hypotensive effects.

Another object of this invention is to provide protoberberine drivatives which exert less depressive effect on the central nervous system than the other related compounds.

Yet another object of the present invention is to provide novel protoberberine derivatives having the general formual (I).

A still further object of the present invention is to provide a process for producing the protoberberine derivatives of the general formula (I).

Briefly, these and other objects of the present invention as hereinafter will become apparent are achieved by providing the protoberberine derivatives of the formula (I) by reacting the compounds of the general formula (II)

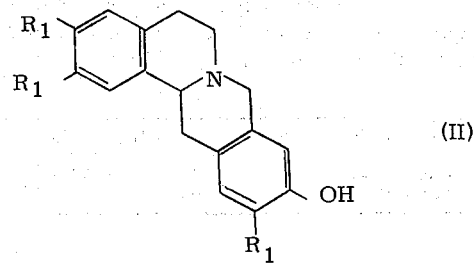

wherein $R_1$ is the same as heretofore defined, with carboxylic acids or reactive derivatives thereof having the general formula (III), $$R_2 - COOH \qquad (III)$$

wherein $R_2$ is the same as heretofore defined.

DETAILED DESCRIPTION OF THE PREFERRED EMBODIMENTS

The known starting compounds having formula (II) may be prepared by well known techniques, such as, by heating 1-(4'-benzyloxy-3'-alkoxybenzyl)-1,2,3,4-tetrahydro-6,7-dialkoxy-isoquinoline with formaline, thereby forming 10-benzyloxy-2,3,11-trialkoxy-5,6,13,13a-tetrahydro-8H-dibenzo[a,g]quinolizine and debenzylating the resulting compound with hydrochloric acid in ethanol.

Suitable compounds having the general formula (II) which may be used include, for example, 10-hydroxy-2,3,11-trimethoxy-5,6,13,13a-tetrahydro-8H-dibenzo-[a, g]quinolizine.

Carboxylic acids having the general formula (III) which may be used include acetic acid, 3,4-dimethoxycinnamic acid, 3,4,5-trimethoxycinnamic acid 3,4,5-trimethoxybenzoic acid and nicotinic acid, and as the reactive derivatives thereof, there may be used the acid anhydrides, acid halides and esters.

In carrying our the process of the present invention, the compound having the formula (II) is reacted with the carboxylic acid of the formula (III) in a suitable solvent, such as pyridine or benzene or the like.

Pharmacological effects of the protoberberine derivatives having formula (I) are as follows:

I. Hypotensive effect.

Two groups of spontaneously hypertensive male rats weighing from 300 to 350 g. (20 to 25 weeks old) were immobilized in a dorsal position, employing no anesthesia, and the blood pressure of the femoral artery was measured by the cannuration method. The percentage variation in the blood pressure of the rats was measured up until 6 hours after medication. The groups consisted of 4 to 6 rats and blood pressure descending curves were drawn and the 20% blood pressure descending dose ($DB_{20}$) was obtained from these curves. Spontaneously hypertensive rats whose systolic pressures were more than 180 mmHg were employed in this experiment. The test materials were injected in the femoral vein.

The results are given in Table I.

| Test Compounds | $DB_{20}$(mg/kg i.v.) |
|---|---|
| 5,6,13,13a-tetrahydro-2,3,11-trimethoxy-10-acetoxy-8H-dibenzo[a, g]-quinolizine | 9.8 |
| 5,6,13,13a-tetrahydro-2,3,10,11,-tetramethoxy-8H-dibenzo[a, g]-quinolizine (known compound) | 4.4 |

2. Enhancing effect on hypnosis of barbital.

A group consisting of ten dd strain male rats weighing from 18 to 22 g. were employed in this experiment. 100 mg/kg of hexobarbital sodium was injected intraperitoneally 30 minutes after intraperitoneal administration of 100 mg/kg of the test materials and thereafter the duration of induced-hypnosis was evaluated by observation of righting reflex.

The results are given in Table 2.

Table 2

| Test Compounds | Duration of hypnosis (minutes) |
| --- | --- |
| 5,6,13,13a-tetrahydro-2,3,11-trimethoxy-10-acetoxy-8H-dibenzo-[a, g] quinolizine | 27 ± 3 |
| 5,6,13,13a-tetrahydro-2,3,10,11-tetramethoxy-8H-dibenzo[a, g]-quinolizine (known compounds) | 99 ± 5 |

As can be clearly seen from Tables 1 and 2, the protoberberine derivatives of the present invention possess a high $DB_{20}$ value while at the same time their depressive effect on the central nervous system is extremely low compared with that of known related compounds. Moreover, the compounds of this invention exhibit a hypotensive effect which bears comparison with that of known related compounds.

Having generally described the invention, a more complete understanding can be obtained by reference to certain specific examples, which are included for purposes of illustration only and are not intended to be limiting unless otherwise specified.

EXAMPLE 1

0.8 g. of 10-hydroxy-2,3,11-trimethoxy-5,6,13,13a-tetrahydro-8H-dibenzo[a, g]quinolizine was dissolved in 8 ml of anhydrous pyridine. To the resulting solution 2 ml of acetic anhydride was added dropwise with stirring, while cooling in an ice-bath. After the mixture was stirred at room temperature for 5 hours, the excessive acetic anhydride was distilled off under reduced pressure, and the residue obtained was extracted with chloroform. The chloroform layer was washed with a 1N-sodium hydroxide solution and then with water, dried over potassium carbonate and evaporated to dryness. Recrystallization of the residue from ethanol-petroleum ether afforded 0.3 g. (33.3% yield) of 5,6,13,13a-tetrahydro-2,3,11-trimethoxy-10-acetoxy-8H-dibenzo [a,g]quinolizine as colorless needles having a melting point of 162° to 164°C.

| Elemental Analysis: | as $C_{22}H_{25}O_5N$ | | |
| --- | --- | --- | --- |
|  | C | H | N |
| Calculated (%) | 68.91 | 6.57 | 3.65 |
| Found (%) | 68.81 | 6.85 | 3.57 |
| IR: $\gamma$ KBr max. | 1765 cm$^{-1}$ (c=o) | | |

EXAMPLE 2

A mixture of 1.9 g of 10-hydroxy-2,3,11-trimethoxy-5,6,13,13a-tetrahydro-8H-dibenzo[a, g]quinolizine hydrochloride, 1.0 g. of nicotinoyl chloride hydrochloride, 2 ml of triethylamine and 150 ml of anhydrous benzene was refluxed in a flask equipped with a tube packed with calcium chloride for 3 hours and then the solvent was distilled off under reduced pressure.

The residue obtained was extracted with chloroform. The chloroform layer was washed with a 1N-sodium hydroxide solution, then with water and dried over potassium carbonate and the solvent was distilled off under reduced pressure. The resulting residue was placed on a column packed with $SiO_2$ and eluted with chloroform. The first 50 ml of effluent was discarded, thereafter the effluent was collected at intervals of 25 ml and there was obtained 2.8 g. of brown glutinous crude product from the combined effluent of fraction numbers 1 to 11 (solidified on trituration with ethyl ether), which was washed with ethyl ether, filtered and dried.

There was obtained 1.1 g. (48.9% yield) of 5,6,13,13a-tetrahydro-2,3,11-trimethoxy-10-nicotinoyloxy-8H-dibenzo[a, g]quinolizine as a pale yellow powder. Because of purification difficulties a part of this was converted to the methiodide thereof and recystallization from a mixture of methanol-ethyl ether afforded a pale yellow powder having a melting point of 223° to 225°C. (decomposition).

| Elemental Analysis: | as $C_{26}H_{26}O_5N_2 \cdot CH_3I \cdot \frac{1}{2}H_2O$ | | |
| --- | --- | --- | --- |
|  | C | H | N |
| Calculated (%) | 54.35 | 5.06 | 4.69 |
| Found (%) | 54.34 | 5.35 | 4.40 |
| IR: $\gamma$ CHCl$_3$ max. | 1740 cm$^{-1}$ (c=o) | | |

EXAMPLE 3

A mixture of the free base obtained from 1.9 g. of 10-hydroxy-2,3,11-trimethoxy-5,6,13,13a-tetrahydro-8H-dibenzo[a, g]quinolizine hydrochloride, 2.0 g. of 3,4,5-trimethoxybenzoyl chloride, 8 ml of triethylamine and 200 ml. of anhydrous benzene was refluxed in a flask equipped with a tube packed with calcium chloride for 7 hours and thereafter the same procedure as followed in Example 2 was repeated. There was obtained 5,6,13,13a-tetrahydro-2,3,11-trimethoxy-10-(3', 4', '-trimethoxybenzoxy)-8H-dibenzo[a, g]quinolizine methiodide as a pale yellow powder having a melting point of 231° to 232°C.

| Elemental Analysis: | as $C_{30}H_{33}O_8N \cdot CH_3I$ | | |
| --- | --- | --- | --- |
|  | C | H | N |
| Calculated (%) | 53.37 | 5.16 | 2.00 |
| Found (%) | 53.44 | 5.35 | 1.73 |
| IR: $\gamma$ CHCl$_3$ max | 1730 cm$^{-1}$ (c=o) | | |

EXAMPLE 4

A mixture of the free base obtained from 1.9 g. of 10-hydroxy-2,3,11-trimethoxy-5,6,13,13a-tetrahydro-8H-dibenzo[a, g]quinolizine hydrochloride, 2.0 g. of 3,4-dimethoxycinnamoyl chloride, 8 ml of triethylamine and 150 ml of anhydrous benzene was refluxed in a flask equipped with a tube packed with calcium chloride for 8 hours and thereafter the same procedure as followed in Example 2 was repeated. There was obtained 5,6,13,13a-tetrahydro-2,3,11-trimethoxy-10-(3', 4'-dimethoxycinnamoyloxy)-8H-dibenzo[a, g]quinolizine methiodide as a pale yellow powder having a melting point of 224° to 225°C.

| Elemental Analysis: | as $C_{31}H_{33}O_7N \cdot CH_3I \cdot 3/2H_2O$ | | |
| --- | --- | --- | --- |
|  | C | H | N |
| Calculated (%) | 54.86 | 5.57 | 2.03 |
| Found (%) | 55.06 | 5.41 | 1.89 |

EXAMPLE 5

A mixture of the free base obtained from 1.9 g. of 10-hydroxy-2,3,11-trimethoxy-5,6,13,13a-tetrahydro-8H-dibenzo[a, g]quinolizine hydrochloride, 2.0 g. of 3,4,5-trimethoxycinnamoyl chloride, 8 ml of triethylamine and 200 ml of anhydrous benzene was refluxed in a flask equipped with a tube packed with calcium chloride for 8 hours, and thereafter the same procedure as followed in Example 2 was repeated. There was obtained 5,6,13,13a-tetrahydro-2,3,11-trimethoxy-10-(3', 4', 5'-trimethoxycinnamoyloxy)-8H-dibenzo[a, g]quinolizine methiodide as a pale yellow powder having a melting point of 207° to 210°C.

| Elemental Analysis: | as $C_{32}H_{35}O_8N \cdot CH_3I$ | | |
|---|---|---|---|
| | C | H | N |
| Calculated (%) | 54.78 | 5.26 | 1.93 |
| Found (%) | 54.52 | 5.40 | 1.63 |
| IR: $\gamma_{max}^{CHCl_3}$ 1720 cm$^{-1}$ (c=o) | | | |

EXAMPLE 6

The free base obtained from 1.9 g. of 10-hydroxy-2,3,11-trimethoxy-5,6,13,13a-tetrahydro-8H-dibenzo[a, g]quinolizine hydrochloride was dissolved in 20 ml of anhydrous pyridine and to the resulting solution 2.0 g. of nicotinoyl chloride hydrochloride was added dropwise with stirring at room temperature. The mixture obtained was stirred for 0.5 hours, followed by a further stirring at 80°C. for 20 hours. After cooling, 50 ml of water was poured into the mixture and the aqueous solution was extracted with chloroform. The chloroform layer was washed with water, dried and the solvent was distilled off. The resulting residue was column chromatographed over 25 g. of SiO$_2$ and eluted with chloroform. The first 50 ml of effluent was discarded, thereafter the effluent was collected at intervals of 50 ml and there was obtained 2.4 g of brown glutinous crude product from the combined effluent (300 ml) of Fraction numbers 1 to 6 (solidified on trituration with ethyl ether), which was collected be filtration, washed with ethyl ether and dried.

There was obtained 0.9 g (40.9% yield) of 5,6,13,13a-tetrahydro-2,3,11-trimethoxy-10-nicotinoyloxy-8H-dibenzo[a, g]quinolizine as a pale yellow powder. The methiodide derived from this compound was found to be in agreement with the methiodide of the compound obtained in Example 2 as determined from the melting point and IR spectrum.

EXAMPLE 7

1.9 g of 10-hydroxy-2,3,11-trimethoxy-5,6,13,13a-tetrahydro-8H-dibenzo[a, g]quinolizine hydrochloride was treated in the same manner as described in Example 6, using 2.0 g of 3,4,5-trimethoxybenzoyl chloride and 200 ml of anhydrous pyridine and there was obtained 1.2 g (44.4% yield) of 5,6,13,13a-tetrahydro-2,3,11-trimethoxy-10-(3', 4', 5'-trimethoxybenzoxy)-8H-dibenzo-[a, g]quinolizine as a pale yellow powder. The methiodide derived from this compound was found to be in agreement with the methiodide of the compound obtained in Example 3 as determined from the melting point and IR spectrum.

EXAMPLE 8

1.9 g of 10-hydroxy-2,3,11-trimethoxy-5,6,13,13a-tetrahydro-8H-dibenzo[a, g]quinolizine hydrochloride was treated in the same manner as described in Example 6, using 2.0 g of 3,4-dimethoxycinnamoyl chloride and 20 ml of anhydrous pyridine and there was obtained 1.0 g (38.4% yield) of 5,6,13,13a-tetrahydro-2,3,11-trimethoxy-10-(3', 4'-dimethoxycinnamoyloxy)-8H-dibenzo[a, g]quinolizine as a pale brown powder. The methiodide derived from this compound was found to be in agreement with the methiodide of the compound obtained in Example 4 as determined from the melting point and IR spectrum.

EXAMPLE 9

1.9 g of 10-hydroxy-2,3,11-trimethoxy-5,6,13,13a-tetrahydro-8H-dibenzo[a, g]quinolizine hydrochloride was treated in the same manner as described in Example 6, using 2.0 g of 3,4,5-trimethoxycinnamoyl chloride and 20 ml of anhydrous pyridine and there was obtained 1.3 g (46.4% yield) of 5,6,13,13a-tetrahydro-2,3,11-trimethoxy-10-(3', 4', 5'-trimethoxycinnamoyloxy)-8H-dibenzo[a, g]quinolizine as a pale yellow powder. The methiodide derived from this compound was found to be in agreement with the methiodide of the compound obtained in Example 5 as determined from the melting point and IR spectrum.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the U.S. is:

1. A protoberbine derivative which is 5,6,13,13a-tetrahydro-2,3,11-trimethoxy-10-acetoxy-8H-dibenzo[a,g]quinolizine.

\* \* \* \* \*